United States Patent [19]

Elsohly et al.

[11] Patent Number: 4,837,228

[45] Date of Patent: Jun. 6, 1989

[54] ANTIINFLAMMATORY AND ANTIMICROBIAL COMPOUNDS AND COMPOSITIONS

[75] Inventors: Mahmoud Elsohly, Oxford, Miss.; Carlton E. Turner, Alexandria, Va.; James C. Murphy, Oxford, Miss.; Phillip W. Wirth, Garland, Tex.

[73] Assignee: The University of Mississippi, University, Miss.

[21] Appl. No.: 404,412

[22] Filed: Aug. 2, 1982

Related U.S. Application Data

[60] Continuation-in-part of Ser. No. 136,554, Apr. 2, 1980, abandoned, which is a division of Ser. No. 44,350, May 31, 1979, Pat. No. 4,315,862.

[51] Int. Cl.[4] .............................................. A61K 31/35

[52] U.S. Cl. .................................................. 514/456

[58] Field of Search ........................... 424/283; 514/456

[56] References Cited

PUBLICATIONS

Kane et al., Jacs, 90: 6551–6553 (1968).

Primary Examiner—Jerome D. Goldberg
Attorney, Agent, or Firm—William D. Stokes

[57] ABSTRACT

The use of cannabichromene (CBC) and its homologues and isomers to induce hypothermia, reduce inflammation in mammals, and as antimicrobial agents is disclosed. Preferably, a compound selected from cannabichromene, its homologues and isomers, is administered as a novel composition, in combination with a pharmaceutically acceptable diluent carrier.

14 Claims, No Drawings

ANTIINFLAMMATORY AND ANTIMICROBIAL COMPOUNDS AND COMPOSITIONS

CROSS-REFERENCE TO A RELATED APPLICATION

This application is a continuation-in-part of Application Ser. No. 136,554, filed Apr. 2, 1980, which Application is a divisional Application filed 5-31-79 of Application Ser. No. 44,350, now U.S. Pat. No. 4,315,862.

BACKGROUND OF THE INVENTION

There have been for many years ongoing searches for the discovery and development of more effective antiinflammatory and hypothermia inducing agents and antimicrobial agents which can be administered to mammals in therapeutically effective dosages with minimal side effects.

A wide variety of compounds having demonstratable antiinflammatory properties are known in the art, for example pyrazolidinediones, arylalkanoic acids, carboxylic acid amides, and salicylates. Anthranilic acid and certain of its derivatives, such as mefenamic acid, flufenamic acid, and N-benzoylanthranilic acid, have also exhibited antiinflammatory activity as described, for example in the article by M. W. Whitehouse, "Biochemical Properties of Anti-Inflammatory Drugs", *Biochem. Pharmacol.*, 16, pp. 753-760 (1967). Aspirin, of course, is probably the most commonly used antiinflammatory and antipyretic agent; however, most of the known antipyretics have the disadvantage of often dangerous side effects from prolonged use such as causing circulatory collapse. There are also known and commonly prescribed antimicrobial agents, for example, streptomycin sulfate and amphotericin B.

Prior to the discovery of the present invention the reported usefulness of cannabichromene was primarily that of an intermediate in the synthesis of related components, for example, cannabicyclol.

SUMMARY OF THE INVENTION

In accordance with this invention cannabichromene, its homologues, and isomers were discovered to be remarkably effective, antiinflammatory and antimicrobial agents in mammals. None of the heretofore known antiinflammatory agents or antimicrobial agents have exhibited the combined therapeutic benefits offered by the compounds and compositions of this invention. The compounds and compositions of the invention may be successfully used to reduce inflammation and to relieve pain in diseases such as arthritis, as well as to reduce and control edema and simultaneously providing treatment as an antibacterial and antifungal agent. The compounds and compositions have exhibited extraordinary inhibition of gram-positive, gram-negative and acid fast bacteria as well as different types of fungi. The compounds and compositions of the invention have also been found to be effective in inducting hypothermia when, for example, a decrease in metabolic activity is desired.

The invention further comprises compounds, compositions and a method for reducing inflammation, inducing hypothermia, and antimicrobial activity in mammals comprising administering cannabichromene, or its homologues, or isomers in a therapeutically effective dose. Treatment for inflammation or to induce hypothermia, or as an antimicrobial may be by any of the conventional routes of administration, for example oral, intramuscular injection, intravenous injection, and/or rectally. The compounds of the invention are preferably administered in combination with a pharmaceutically-acceptable carrier which may be solid or liquid. Examples of acceptable solid carriers include, but are not limited to, starch, dextrose, sucrose, lactose, gelatin, agar, stearic acid, magnesium stearate, acacia, and similar carriers. Examples of liquids include, but are not limited to, water, edible oils, such as corn or peanut oils, and the like.

When administered in solid form, the compound and diluent carrier may be in the form of tablets, capsules, powders or lozenges prepared by standard techniques. When given as a liquid preparation, the mixture of active compound and liquid diluent carrier may be in the form of a liquid suspension administered as such or encapsulated.

When employed to treat an inflammatory condition and/or a bacterial or fungal infection in a mammal, animla, or human, the active compound is preferably administered orally in admixture with a pharmaceutically-acceptable diluent carrier as described above. When employed to induce hypothermia in a mammal, animal or human, the active compound is preferably administered by intraperitoneal injection, also an admixture with a pharmaceutically acceptable diluent carrier as described above. The compound is administered in a non-toxic dosage concentration sufficient to reduce the inflammation or edema where present, or to induce the desired degree of hypothermia. The actual dosage administered will be determined by such generally-recognized factors as the body-weight of the subject, the severity of the condition being treated, the idiosyncrasies of the particular subject, and the activity of the compound employed. With these considerations in mind, the dosage for a particular subject can be readily determined by the medical practitioner in accordance with conventional techniques in the medicinal art.

Compounds used in the inventive compounds and compositions are simply advantageously prepared by the method of Elsohly et al described in U.S. Pat. No. 4,315,862 and as described hereinafter.

DETAILED DESCRIPTION OF THE INVENTION

Cannabichromene, the homologues and the isomers of the present invention were prepared by condensation of olivetol, orcinol and resorcinol with citral, respectively, following the teaching of U.S. Pat. No. 4,315,862 for synthesis of cannabichromene. For ready reference, the structural formulae of the compounds of the invention are as follows:

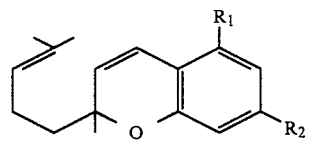

wherein $R_1$ is hydrogen, $C_1$–$C_{10}$-alkyl or $C_2$–$C_{10}$ alkenyl and $R_2$ is hydroxy, or, where in $R_2$ is hydrogen, $C_1$–$C_{10}$-alkyl or $C_2$–$C_{10}$-alkenyl and $R_1$ is hydroxy and the di- or tetrahydro derivative thereof.

Specific compounds of the invention which were prepared and tested were
(I) 2-methyl-2(4'methyl-pent-3'-enyl)-5-hydroxy-7-pentyl chromene;

(II) 2 methyl-2(4'-methyl-pent-3'-enyl)-5-hydroxy-7-metylchromene;
(III) 2-methyl-2(4'-methyl-pent-3'-enyl)-5-methyl-7-hydroxychromene;
(IV) 2-methyl-2(4'-methyl-pent-3'-enyl)-5-hydroxy-7-methyl chroman;
(V) 2-methyl-2(4'-methyl-pentyl)-5-hydroxy-7-methyl chroman;
(VI) 2-methyl-2-(4'-methyl-pent-3'-enyl)-5-hydroxy-chromene;
(VII) 2-methyl-2(4'-methyl-pent-3'-enyl)-7-hydroxy-chromene;
(VIII) 2-methyl-2(4'-methyl-pent-3'-enyl)-5-hydroxy-7-pent-dec-8'-enyl chromene;
(IX) 2-methyl-2(4'-methyl-pent-3'-enyl)-5-pentyl-7-hydroxy chromene;
(X) 2-methyl-2(4'-methyl-pentyl)-5-hydroxy-7-pentyl chroman.

In the testing described herein the compounds and compositions of the invention were administered using two routes, intraperitoneal and oral. The compounds of the invention were administered in combination with a pharmaceutically acceptable carrier. As discussed hereinbefore it is understood that the carrier may be solid or liquid, solely depending upon the route of administration. Examples of suitable carriers include, but are not limited to, starch, dextrose, sucrose, lactose, gelatin, agar, stearic acid, magnesium, stearate and acacia. Examples of suitable liquid carriers are water, edible oils, isotone solutions, and the like. When administered in solid form, the compounds and compositions of the invention my be in the form of tablets, capsules, powders and lozenges prepared by standard techniques. When given as a liquid preparation, the composition may be in the form of a liquid suspension administered as such or encapsulated.

A determination of acute $LD_{50}$ of the compounds and compositions of the invention was made using ICR mice weighing 30 to 50 Gm using two routes of administration—subcutaneous and oral. The compositions were emulsified with gum acacia and olive oil in water. The treated mice were observed for two weeks. No lethality of the compositions was observed.

Two methods were used to assess the antiinflammatory activity of the compounds of the invention: the carrageenan-induced rat paw edema test and, the erythrocyte membrane stabilization assay. Utilizing either test, the compounds of the invention were found to be more effective than the standard treatment utilizing phenylbutazone in controlling inflammation.

INHIBITION OF INFLAMMATION MEASURED BY RAT PAW EDEMA TEST

In the Rat Paw Edema Test, the rats utilized were divided into test groups of six to eight animals, weighed and marked so that individual rats could be identified; one hour before testing all rats were given a 700 mg/kg intraperitoneal injection of ethyl urethane in distilled water to render them tractable during testing. A circle was drawn, with a felt-tipped marker, around the hind leg of each rat just above the ankle, and each rat was dosed with a test or control compound by intraperitoneal injection. Negative control groups received the vehicle; while positive control groups received a dose of phenylbutazone (PBZ) as shown in Table II. Test compounds were given at doses of 60, 120, 240 and 480 mg/kg. The positive controls were given at 120 mg/kg and 60 mg/kg. Phenylbutazone was prepared for injection by suspending it in normal saline using Tween 60. The rats were then held in group cages for 30 minutes. The volume of the left hind paw was measured using a mercury displacement pleysmograph. The paw is dipped into the mercury until the mercury touches the line above the ankle. Mercury is then withdrawn until the mercury returns to its original level. The amount of mercury removed is measured in milliliters (ml). The mercury can be measured accurately to 0.01 ml. This left hind paw was then injected with 0.1 ml of a 5% w/v solution of viscous carageenan in normal saline. The injection was given between the metatarsal bones using a 27 gauge needle, and the rats then held in group cages for 3 hours. The volume of the left hind paws was measured again in the pleysmograph. The results were computed in the following manner:

a. A mean is taken for both the pre-injection and post-injection paw volume of each test group.
b. The mean difference in volume (MDV) for each test group is computed by subtracting the pre-injection means from the post-injection mean.
c. The percent of control is computed for each test $$\% \text{ of control} = \frac{MDV \text{ control group}}{MDV \text{ test group}} \times 100$$

The percent of control is used to compare the efficacy of the various drug treatments.

d. The percent increase in paw volume is calculated for each group as:

$$\% \text{ increase} = \left(\frac{\text{Post-injection Mean}}{\text{Pre-injection Mean}} \times 100\right) - 100$$

The percent increase is used to compare the amount of edma observed in one experiment to the amount of edma observed in other experiments.

The results of one series of tests using the rat paw edema test are summarized in Table 1. As can be seen, doses of 120, 240, and 480 mg/kg all produced strong antiinflammatory effects. The effects were shown to be dose related, that is, higher doses of CBC produced stronger antiinflammatory effects. All the animals receiving 480 mg/kg died within 2 days of injection, but this cannot be judged to be simply a result of CBC toxicity since the rats also received an IP injection of 750 mg/kg of ethyl urethane as part of the test procedure. Seven of the eight animals receiving 240 mg/kg of PBZ died before the test could be completed. The eighth rat died within 24 hours of injection.

The data from the rat paw test were further analyzed using a one-way analysis of varience (ANOVA) and Duncan's New Multiple Range Test. The results of these tests are given in Tables 2 and 3. The pre-injection score of each animal was subtracted from his post-injection score and an analysis of the different scores were conducted. The analysis showed that all test groups differed significantly from the vehicle control group. The 120 mg/kg dose of CBC differed significantly from the 240 and 480 mg/kg doses of CBC, and the 480 mg/kg dose of CBC differed significantly from the 120 mg/kg dosage of PBZ.

No significant effects were seen on the CNS screen at doses of CBC as large as 800 mg/kg in unanesthetized mice.

The procedure described above was followed. CBC(II) was tested at doses of 60 mg/kg and 120 mg/kg prepared in an emulsion with Tween 60, Arlacel and distilled water. The vehicle control used was Tween 60, Arlacel and distilled water prepared without CBC(II).

The results are given in Table 4. CBC(II) was active at both 60 mg/kg and 120 mg/kg. The inhibition of edema was dose related. When the effects of CBC(II) were compared with those of PBZ it can be seen that CBC(II) did reduce the rat paw edema with slightly less activity than PBZ at the 120 mg/kg dose and was as active at PBZ at 60 mg/kg. No toxic or adverse effects were observed in any of the rats tested.

Table 5 is a summary of the results of another series expressed in percentage inhibition. The dosage units for this test was 60, 120, 240 and 480 mg/kg. As may be seen from the results as compared with phenylbutazone all dosage levels exhibited remarkable antiinflammatory activity. These tests in which the compounds were administered intraperitoneally and also orally to both fasted and non fasted rats reveal that the other compounds are more active when administered by the intraperitoneal route.

TABLE 1

RAT - PAW EDEMA DATA

| COMPOUND | DOSE | MDV | PERCENT OF CONTROL | PERCENT INCREASE |
|---|---|---|---|---|
| Vehicle Control | 0.00 MG/KG | 0.463 | 100.000 | 42.383 |
| CBC | 120 MG/KG | 0.139 | 30.000 | 12.729 |
| CBC | 240 MG/KG | 0.004 | 0.927 | 0.365 |
| CBC | 480 MG/KG | −0.043 | −9.189 | −3.708 |
| PBZ | 120 MG/KG | 0.106 | 22.973 | 10.316 |

Percent of Control and Percent Increase Computed Before Rounding MDVS or Group Means.

TABLE 2

Analysis of varience for difference scores from rat-paw edema test of Table 1

| Source | $\Sigma X^2$ | df | MS | F |
|---|---|---|---|---|
| Among | 1.2291 | 4 | 0.3073 | 24.434** |
| Within | 0.4311 | 34 | 0.0128 | |
| Total | 1.6602 | 38 | | |

TABLE 3

Duncan's Test for Difference Scores Rat-Paw Edema Test as shown in Table 1

| Group | $\bar{x}$ | $I_0$ | $I_1$ | $I_2$ | $I_3$ | SSR+ |
|---|---|---|---|---|---|---|
| Vehicle control | 0.463 | — | 0.324** | 0.356** | 0.458** | 0.505** | 0.170 |
| | | | | | | | 0.128 |
| CBC 120 mg/kg | 0.139 | — | — | 0.033 | 0.134* | 0.181** | 0.167 |
| | | | | | | | 0.125 |
| PBZ 120 mg/kg | 0.016 | — | — | — | 0.102 | 0.149* | 0.162 |
| | | | | | | | 0.121 |
| CBC 240 mg/kg | 0.004 | — | — | — | — | 0.047 | 0.156 |
| | | | | | | | 0.115 |
| CBC 480 mg/kg | 0.043 | — | — | — | — | — | |
| | | Vehicle control | CBC 120 mg/kg | PBZ 120 mg/kg | CBC 240 mg/kg | CBC 480 mg/kg | |

*p. 0.05
**p. 0.01
+Shortest significant range for the 0.05 and 0.01 levels of significance.

TABLE 4

RAT - PAW EDEMA DATA
$CBC-C_1$ given i.p. in fasted rats. Run 5-10-79

| COMPOUND | DOSE | MDV | PERCENT OF CONTROL | PERCENT INCREASE |
|---|---|---|---|---|
| Vehicle Control | 0.00 MG/KG | 0.191 | 100.000 | 13.947 |
| $CBC-C_1$ | 120 MG/KG | 0.070 | 36.601 | 4.956 |
| $CBC-C_1$ | 60 MG/KG | 0.090 | 47.059 | 6.742 |
| PBZ | 120 MG/KG | 0.046 | 24.183 | 3.254 |
| PBZ | 60 MG/KG | 0.090 | 47.059 | 6.742 |

Percent of Control and Percent Increase Computed Before Rounding MDVS or Group Means.

TABLE 5

INHIBITION OF CARRAGEENAN-INDUCED RAT PAW EDEMA
BY CANNABICHROMENE AND ITS C1-HOMOLOG

| Compound | Dose (mg/kg) | Route of administration | Inhibition (%) |
|---|---|---|---|
| CBC (IV) | 120 | intreperitoneal injection | 70* |
| | 240 | intraperitoneal injection | 86* |
| | 480 | intraperitoneal injection | 100 |
| CBC (V) | 60 | intraperitoneal injection | 53* |
| | 120 | intraperitoneal injection | 63* |
| | 240 | intraperitoneal injection | 92* |
| Phenylbutazone | 60 | intraperitoneal injection | 52* |
| | 120 | intraperitoneal injection | 76* |
| CBC (IV) | 120 | oral, fasted rats | 35 (N.S.) |
| | 240 | oral, fasted rats | 67* |
| | 480 | oral, fasted rats | 55** |
| Phenylbutazone | 120 | oral, fasted rats | 36 (N.S.) |
| CBC (IV) | 120 | oral, nonfasted rats | 21 (N.S.) |
| | 240 | oral, nonfasted rats | 34** |
| | 480 | oral, nonfasted rats | 50* |
| Phenylbutazone | 60 | oral, nonfasted rats | 37* |
| | 120 | oral, nonfasted rats | 22* |

*P = 0.01
**P = 0.05

INHIBITION OF INFLAMMATION BY CBC AS MEASURED BY THE RAT EDEMA TEST (ORAL ADMINISTRATION)

The procedure described hereinabove with respect to Tables 1–5 was followed, except the rats were dosed solely by oral gavage instead of i.p. injection. The test was conducted twice, once with nonfasted rats and once with rats that had been fasted during the 24 hour period prior to dosing. The 60 mg/kg phenylbutazone control group was not used in the test with fasted animals. Tween 60 in normal saline was the vehicle control for the non-fasted rats and normal saline was the vehicle control for the fasted rats.

The results were given in Tables 6 and 7. As may be seen from the tables, the inventive compounds were active at all the doses tested. The degree of inhibition of edema increased in both tests as the amount of compound given was increased. The degree of inhibition was greater in the fasted rats than it was in the nonfasted rats. This would be expected since the fasted rats should absorb the test compound more readily than the non-fasted rats.

When the compound is compared to PBZ in Tables 1 and 2 it is seen that PBZ was slightly more effective than CBC at 120 mg/kg in the nonfasted rats and that CBC and PBZ were about equally effective at 120 mg/kg in the fasted rats. The higher doses of CBC were generally more effective in inhibiting edema than was PBZ. PBZ was not given at higher doses because of the rapid deaths produced by 240 mg/kg of PBZ given intraperitoneally in the test described hereinbefore.

TABLE 6
RAT - PAW EDEMA DATA
Oral CBC in Non-Fasted Rats. Run 11-6-1978

| COMPOUND | DOSE | MDV | PERCENT OF CONTROL | PERCENT INCREASE |
|---|---|---|---|---|
| Vehicle Control | — | 0.625 | 100.000 | 58.140 |
| CBC | 120 MG/KG | 0.496 | 79.400 | 41.311 |
| CBC | 240 MG/KG | 0.412 | 66.000 | 38.372 |
| CBC | 480 MG/KG | 0.315 | 50.400 | 29.200 |
| PBZ | 60 MG/KG | 0.489 | 78.200 | 50.257 |
| PBZ | 120 MG/KG | 0.392 | 62.667 | 36.098 |

Percent of Controls and Percent Increase Computed Before Rounding MDVS or Group Means.

TABLE 7
RAT - PAW EDEMA DATA
Oral CBC in Fasted Rats. Run 11-14-1978

| COMPOUND | DOSE | MDV | PERCENT OF CONTROL | PERCENT INCREASE |
|---|---|---|---|---|
| Saline Vehicle Control | 120 MG/KG | 0.625 | 100.000 | 46.339 |
| CBC | 120 MG/KG | 0.409 | 65.400 | 31.382 |
| CBC | 240 MG/KG | 0.209 | 53.400 | 15.981 |
| CBC (given following saline infusion) | 480 MG/KG | 0.281 | 45.000 | 22.321 |
| PBZ | 120 MG/KG | 0.403 | 64.400 | 31.051 |

Percent of Control and Percent Increase Computed Before MDVS or Group Means.
*Doses are Approximate Due an Error in PR.

INHIBITION OF INFLAMMATION BY CBC AS MEASURED BY INHIBITION OF ERYTHEMA

(ERYTHROCYTE MEMBRANE STABILIZATION ASSAY)

The published procedure (Proc. Soc. Exp. Biol. Med. 1967; 125; 837–842 Brow et al) for in vitro assay for antiinflammatory agents based on stabilization of erythrocytes was used. All compounds were prepared for administration by dissolving in physiologic saline or suspending in 2% ethanol in saline and the pH adjusted to 7.4 The concentrations tested in one series are given in Table 8. Aspirin (ASA) and phenylbutazone were used as positive controls for comparison of activity. Tests using this procedure were successfully and repeatedly using either 40% or 20% RBC suspensions.

Another series of tests are reported in Table 9. Phenylbutazone (PBZ), aspirin and tolmetin were used as positive controls and all inhibited heat induced hemolysis at the concentration tested. Inhibition of hemolysis was dose-related in the positive controls and cannabichromene groups (Test 3). CBC produced 35% inhibition of heat-induced red cell hemolysis at $10^{-4}$M test concentration and 26% at $2\times10^{-5}$M CBC. PBZ produced 16% and 10% inhibition of red cell hemolysis at the $10^{-4}$M and $2\times10^{-5}$M test levels, respectively. Aspirin produced a 40% inhibition at the $5\times10^{-4}$M test concentration.

It was apparent that not all the CBC actually went into suspension. In order to determine if some of the CBC adhered to the wall of the glassware a 10 ml aliquot of the $2\times10^{-4}$ (solution a) of CBC saturated with NaCl was extracted with CHCl$_3$ and analyzed by G.C. The solution was found to be $2\times10^{-5}$M CBC or to contain 0.3 mg of the original CBC. The flask was rinshed with ethanol and the washings analyzed by G.C. and found to contain 1.355 mg of CBC. The remaining 1.475 mg (50%) of CBC that could not be accounted for by G.C. analysis may have been lost during the extraction procedure or while adjusting the pH of the test solution. If the 1.475 mg CBC which could not be accounted for was actually in suspension then the maximum final concentration of CBC used in the highest CBC test level would be $5\times10^{-5}$M or one half the amount listed in Table 6. In summary, CBC, at a minimum, produces 2 to 2½ times more inhibition of heat induced red cell hemolysis than does PBZ at equimolar concentrations. Inhibition of heat-induced hemolysis was seen over a range of $10^{-4}$M to $2\times10^{-6}$M CBC. The actual activity of CBC may have been 3 to 30 times more protective of red cell membranes than an equivalent amount of PBZ.

TABLE 8
INHIBITION OF HEAT-INDUCED ERYTHROCYTE HEMOLYSIS BY CANNABICHROMENE AND ITS HOMOLOGS AND ISOMERS

| Compound | Concentration of Test Solution (M) | Inhibition (%) |
|---|---|---|
| Cannabichromene (IV) | $1 \times 10^{-4}$ | 98 |
| | $5 \times 10^{-5}$ | 79 |
| | $2.5 \times 10^{-5}$ | 67 |
| | $1.25 \times 10^{-5}$ | 55 |
| Isocannabichromene (VII) | $1 \times 10^{-4}$ | 75 |
| Cannabichromene-C$_1$ (V) | $1 \times 10^{-4}$ | 86 |
| Cannabichromene-C$_o$ (VI) | $1 \times 10^{-4}$ | 69 |
| Isocannabichromene-C$_o$ (VIII) | $1 \times 10^{-4}$ | 43 |
| Phenylbutazone | $1 \times 10^{-4}$ | 16 |
| | $2 \times 10^{-5}$ | 10 |
| Aspirin | $2.5 \times 10^{-4}$ | 21 |

TABLE 9
(Inhibition of Heat-Induced Erythrocyte Hemolysis)

| Final Concentration of the TEST SOLUTION | Percent Inhibition | | |
|---|---|---|---|
| | TEST 1* | TEST 2 | TEST 3 |
| Phenylbutazone | | | |
| $2.5 \times 10^{-4}$ M | 54 | 70 | 49 |
| $1.0 \times 10^{-4}$ M | | | 16 |
| $2.5 \times 10^{-5}$ M | 31 | | |
| $2.0 \times 10^{-5}$ M | | | 10 |
| Acetylsalicylic Acid | | | |
| $5.0 \times 10^{-4}$ M | | | 40 |
| $2.5 \times 10^{-4}$ M | 21 | | |

TABLE 9-continued (Inhibition of Heat-Induced Erythrocyte Hemolysis)

| Final Concentration of the TEST SOLUTION | Percent Inhibition | | |
|---|---|---|---|
| | TEST 1* | TEST 2 | TEST 3 |
| Tolmetin | | | |
| $2.0 \times 10^{-4}$ M | 27 | | |
| Cannabichromene | | | |
| $1.0 \times 10^{-4}$ M | | 40 | 37 |
| $1.0 \times 10^{-4}$ M | | | 33 |
| $2.0 \times 10^{-5}$ M | | 26 | 26 |
| $2.0 \times 10^{-6}$ M | | | 7 |

*A 20% RBC suspension was used for Tests 1 and 3.
A 40% RBC solution was used for Test 2.

INDUCEMENT OF HYPOTHERMIA BY CBC IN MICE

CBC (100 mg/kg) was prepared in emulsion form with 3% Tween 60 and 3% Arlacel in normal saline (0.9%) in such a way as to permit a volume of 10 mg/kg of body weight to be injected intraperitoneally into male mice weighing between 32 and 38 grams.

The animals were divided into groups of 10, and body temperatures were recorded with a multichannel Yellow Springs Telethermometer and Thermistor probes. During the experiment, the mice were confined in plastic restraint tubes. They were allowed 45–60 min. for adaption to the restraint tubes and to rectal thermister before a pre-drug baseline temperature reading was taken. Body temperature readings were obtained at 0.5, 1.0, 2.0, 3.0 and 4.0 hrs. post-CBC administration.

The mean ($\pm$S.E.) decrease in temperature from the preinjection baseline reading for saline-, vehicle-, and CBC-treated mice were calculated and statistical analyses were conducted using the the two-tailed Student's t test.

As summarized in Table 10, both the CBC- and vehicle control-treated groups showed a consistent drop in body temperature over the duration of the experiment, with the CBC-induced hypothermia being more pronounced and significantly different from saline controls at all readings whereas the vehicle indicated decrease in body temperature was only significant from saline controls at the 2.0, 3.0 and 4.0 hr. readings.

In spite of the vehicle's activity, the hypothermia induced by CBC was still significantly different from vehicle controls at 0.5, 1.0 and 4.0 hrs.

The peak hypothermic effect (at a dose of 100 mg/kg, i.p.) for CBC was attained within the first two hours and then declined thereafter.

ANTIMICROBIAL EFFECTS

An antimicrobial activity was determined by screening the compounds of the invention against the organisms listed in Table 11. Both qualitative and quantitative screens were performed. Qualitative screening was accomplished using the agar well diffusion assay technque while quantitative screening was accomplished by the two-fold (broth) serial dilution method to determine the minimum inhibitory concentration (MIC). Innoculation was accomplished with one loop-full of a 1:10 dilution of the 24-hour-old broth culture, (fungal cultures and M.smegmatis more often required 48 to 72 hours of incubation) of the test organisms in sterile water. Streptomycin sulfate was used as a positive control for antibacterial activity while amphitericin B was used as an antifungal positive control. The compounds were subjected to centibacterial and antifungal activity screens as summarized in Tables 12–15. Organisms utilized in the screens included gram-positive, gram-negative, and acid-fast bacteria as well as different types of fungi. Qualitative screening using the agar well diffusion assay showed that these compounds possess strong antimicrobial properties. The compounds exhibited large zones of inhibition when compared to positive standards at the same concentrations. The minimum inhibitory concentrations (MIC) for these compounds were determined using selected bacteria and fungi as recorded in Tables 14 and 15. The organisms selected from the MIC determination were based on the largest zone of inhibition resulting from the qualitative screens set out in Tables 12 and 13. The compounds of the invention where R is a methyl or a pentyl group exhibit the highest antimicrobial activity. An intermediate type activity is seen where R is hydrogen. However, where R is lengthened up to $C_{15}$ a decrease in activity was noted. Total saturation of the two double bonds in the compounds having a methyl side chain lead, in most cases, to an increase in both antifungal and antibacterial activity.

TABLE 11

ANTIMICROBIAL SCREENING USING THE AGAR WELL DIFFUSION ASSAY

| Organism | ATCC # | Classification |
|---|---|---|
| Bacillus subtilis | 6633 | gram-positive bacterium |
| Staphylococcus aureus | 6538 | gram-positive bacterium |
| Escherichia coli | 10536 | gram-negative bacterium |
| Pseudomonas aeruginosa | 15442 | gram-negative bacterium |
| Mycobacterium smegmatis | 607 | acid-fast bacterium |
| Candida albicans | 10231 | yeast-like fungus |
| Saccharomyces cerevisiae | 9763 | yeast-like fungus |
| Aspergillus niger | 16888 | filamentous fungus |
| Trichophyton mentagrophytes | 9972 | dermatophyte |

TABLE 10

| | Mean ($\pm$S.E.) Decrease in Rectal Temp. (°0) | | | | |
|---|---|---|---|---|---|
| | Time (hrs.) | | | | |
| Treatment | 0.5 | 1.0 | 2.0 | 3.0 | 4.0 |
| Normal Saline | 0.43 $\pm$ 0.12 | 0.44 $\pm$ 0.07 | 0.47 $\pm$ 0.07 | 0.61 $\pm$ 0.14 | 0.60 $\pm$ 0 |
| Vehicle Control | 0.58 $\pm$ 0.16 | 0.80 $\pm$ 0.16 | 1.62 $\pm$ 0.16* | 1.35 $\pm$ 0.14* | 1.04 $\pm$ 0Δ |
| CBC (100 mg/kg) | 1.86 $\pm$ 0.18Δ* | 2.52 $\pm$ 0.26Δ* | 1.93 $\pm$ 0.21* | 1.53 $\pm$ 0.21* | 1.61 $\pm$ 0 |

*Significantly different from saline controls, P $\leq$ 0.05.
ΔSignificantly different from vehicle control, P $\leq$ 0.05.

TABLE 12

MINIMUM INHIBITORY CONCENTRATION (MIC) OF CANNABICHROMENE AND ITS HOMOLOGS AND ISOMERS AGAINST DIFFERENT ORGANISMS

| | MIC (µg/ml) | | | | | | | | | |
|---|---|---|---|---|---|---|---|---|---|---|
| | B. subtilis | | S. aureus | | M. smegmatis | | E. coli | | Ps. aeruginosa | |
| Compound | 24 hr. | 48 hr. | 24 hr. | 48 hr. | 24 hr. | 48 hr. | 24 hr. | 48 hr. | 24 hr. | 48 hr. |
| CBC (IV) | 0.39 | 0.78 | 1.56 | 1.56 | 12.5 | 25.0 | — | — | — | — |
| Iso CBC (VII) | 0.78 | 3.12 | NT | NT | 25.0 | 25.0 | — | — | — | — |
| CBC (VI) | 6.25 | 12.5 | 12.5 | 12.5 | 12.5 | 12.5 | — | — | — | — |
| Streptomycin SO$_4$ | 6.25 | 25 | 3.12 | 12.5 | 1.56 | 1.56 | — | — | — | — |
| CBC (V) | 3.12 | 3.12 | 3.12 | 3.12 | 3.12 | 6.25 | — | — | — | — |
| CBC (VIII) | 6.25 | 6.25 | 12.5 | 12.5 | 12.5 | 12.5 | — | — | — | — |
| Streptomycin SO$_4$ | 3.12 | 6.25 | 6.25 | 6.25 | 6.25 | 6.25 | — | — | — | — |
| CBC (IV) | 8.0 | 5.0 | 10. | 10. | 15. | 12. | 5. | 5. | 1. | 1. |
| CBC (V) | 16.0 | 9.0 | 25. | 25. | 25. | 25. | 5. | 5. | 4. | 3. |
| CBC (X) | 4.0 | 4.0 | 13. | 13. | 7. | 7. | 5. | 5. | 1. | 1. |
| Iso CBC (VIII) | — | — | 10. | 10. | 5. | 5. | — | — | 4. | 4. |
| Streptomycin SO$_4$ | 7. | 8. | 9. | 9. | 20. | 22. | 2. | 2. | 3. | 3. |
| Iso CBC (VII) | 10. | 7. | — | — | 6. | 4. | 2. | 2. | — | — |
| CBC (VI) | 10. | 10. | 15. | 15. | 20. | 18. | 3. | 2. | 3. | — |
| Streptomycin-SO$_4$ | 11. | 10. | 10. | 10. | 20. | 22. | 5. | 5. | 7. | 6. |

Streptomycin-SO$_4$ was used as standard.
*Antimicrobial activity was recorded as the width (in mm) of the inhibition zone measured from the edge of the agar well to the edge of the inhibition zone.

TABLE 13

MINIMUM INHIBITORY CONCENTRATION (MIC) OF CANNABICHROMENE AND ITS HOMOLOGS AND ISOMERS AGAINST DIFFERENT FUNGI

| | MIC (µg/ml) | | | | | | | |
|---|---|---|---|---|---|---|---|---|
| | C. albicans | | S. cervisiae | | T. mentagrophytes | | A. niger | |
| Compound | 48 hr. | 72 hr. | 48 hr. | 72 hr. | 48 hr. | 72 hr. | 48 hr. | 72 hr. |
| CBC (IV) | NT | NT | 25 | 50 | 25 | 50 | — | — |
| Amphotericin B* | NT | NT | 3.12 | 3.12 | NT | NT | — | — |
| Iso CBC (VII) | 50 | 100 | NT | NT | NT | NT | — | — |
| CBC (VI) | 50 | 50 | 25 | 25 | 25 | 25 | — | — |
| Amphotericin B* | 1.56 | 1.56 | 0.78 | 0.78 | NT | NT | — | — |
| CBC (V) | NT | NT | 6.25 | 12.5 | 6.25 | 6.25 | — | — |
| Iso CBC (VIII) | 12.5 | 25 | NT | NT | 6.25 | 6.25 | — | — |
| Amphotericin B* | 1.56 | 6.25 | 0.19 | 0.78 | 12.5 | 25 | — | — |
| CBC (IV) | 4.0 | 4.0 | 8. | 8. | No growth | | 2. | 2. |
| CBC (V) | 3.0 | 3.0 | 22. | 22. | No growth | | 3. | 3. |
| CBC (X) | 2. | 3. | 7. | 7. | No growth | | 1. | 1. |
| Iso CBC (VIII) | 4. | 5. | 4. | 4. | No growth | | 1. | — |
| Amphotericin B | 7. | 8. | 7. | 8. | No growth | | 4. | 4. |
| Iso CBC (VII) | 3. | 2. | 2. | 2. | No growth | | — | — |
| CBC (VI) | 7. | 5. | 10. | 8. | 20. | 19. | 9. | 5. |
| Amphotericin B | 5. | 3. | 7. | 5. | 4. | 4. | 2. | 1. |

*Antimicrobial activity was recorded as the width (in mm) of the inhibition zone measured from the edge of the agar well to the edge of the inhibition zone.

TABLE 14

**MINIMUM INHIBITORY CONCENTRATION (MIC)* OF CANNABICHROMENE AND CANNABIGEROL HOMOLOGS AND ISOMERS AGAINST DIFFERENT ORGANISMS**

| | B. subtilis | | S. aureus | | M. smegmatis | |
|---|---|---|---|---|---|---|
| Compound | 24 hr. | 48 hr. | 24 hr. | 48 hr. | 24 hr. | 48 hr. |
| CBC (I) | 0.39 | 0.78 | 1.56 | 1.56 | 12.5 | 25.0 |
| Iso CBC (IX) | 0.78 | 3.12 | NT | NT | 25.0 | 25.0 |
| CBC (VI) | 6.25 | 12.5 | 12.5 | 12.5 | 12.5 | 12.5 |
| Streptomycin-SO$_4$ | 6.25 | 25.0 | 3.12 | 12.5 | 1.56 | 1.56 |
| CBC (II) | 3.12 | 3.12 | 3.12 | 3.12 | 3.12 | 6.25 |
| Iso CBC (VII) | 6.25 | 6.25 | 12.5 | 12.5 | 12.5 | 12.5 |
| Streptomycin-SO$_4$ | 3.12 | 6.25 | 6.25 | 6.25 | 6.25 | 6.25 |
| CBC (V) | 1.56 | 1.56 | 0.78 | 3.12 | 3.12 | 3.12 |
| Streptomycin-SO$_4$ | 12.5 | 100 | 25.0 | 25.0 | 6.25 | 6.25 |
| CBC (VIII) | 50 | 50 | 50 | 100 | 25 | 50 |
| Streptomycin-SO$_4$ | 6.25 | 6.25 | 6.25 | 25 | 0.78 | 0.78 |

*Expressed in µg/ml
NT: Not tested

TABLE 15

**MINIMUM INHIBITORY CONCENTRATION (MIC)* OF CANNABICHROMENE AND CANNABIGEROL HOMOLOGS AND ISOMERS AGAINST DIFFERENT FUNGI**

| | C. albicans | | S. cervisiae | | T. mentagrophytes | | A. niger | |
|---|---|---|---|---|---|---|---|---|
| Compound | 48 hr. | 72 hr. | 48 hr. | 72 hr. | 48 hr. | 72 hr. | 48 hr. | 72 hr. |
| CBC (I) | NT | NT | 25.0 | 50.0 | 25.0 | 50.0 | | |
| Amphotericin B | NT | NT | 3.12 | 3.12 | NT | NT | | |

TABLE 15-continued

MINIMUM INHIBITORY CONCENTRATION (MIC)* OF
CANNABICHROMENE AND CANNABIGEROL HOMOLOGS AND
ISOMERS AGAINST DIFFERENT FUNGI

| Compound | C. albicans 48 hr. | C. albicans 72 hr. | S. cervisiae 48 hr. | S. cervisiae 72 hr. | T. mentagrophytes 48 hr. | T. mentagrophytes 72 hr. | A. niger 48 hr. | A. niger 72 hr. |
|---|---|---|---|---|---|---|---|---|
| Iso CBC (IX) | 50.0 | 100 | NT | NT | NT | NT | | |
| CBC (VI) | 50.0 | 50.0 | 25.0 | 25.0 | 25.0 | 25.0 | | |
| Amphotericin B | 1.56 | 1.56 | 0.78 | 0.78 | NT | NT | | |
| CBC (II) | NT | NT | 6.25 | 12.5 | 6.25 | 6.25 | | |
| Iso CBC (VII) | 12.5 | 25.0 | NT | NT | 6.25 | 6.25 | | |
| Amphotericin B | 1.56 | 6.25 | 0.19 | 0.78 | 12.5 | 25.0 | | |
| CBC (V) | NT | NT | 12.5 | 12.5 | 50.0 | 50.0 | | |
| Amphotericin B | NT | NT | 6.25 | 6.25 | 25.0 | 25.0 | | |
| CBC (VIII) | 50 | 100 | 100 | 100 | 25 | 50 | | |
| Amphotericin B | 12.5 | 25 | 3.12 | 6.25 | 6.25 | 50 | | |

*Expressed in μg/ml
NT: Not tested

Although this invention has been described with reference to illustrate embodiments thereof, it will be apparent to those skilled in the art that the principles of this invention will be embodied in other forms within the scope of the following claims.

What is claimed is:

1. A method of reducing inflammation in mammals comprising administering to said mammals a composition consisting essentially of a compound of the formula

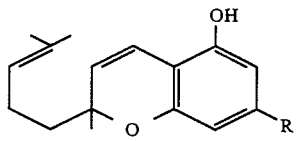

wherein R is hydrogen, $C_1$-$C_{10}$-alkyl, or $C_2$-$C_{10}$-alkenyl in a therapeutically effective amount and a non-toxic, pharmaceutically acceptable carrier.

2. A method for inducing hypothermia in mammals comprising administering to said mammals a composition consisting essentially of a compound of the formula

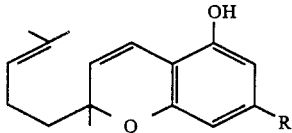

where R is hydrogen, $C_1$-$C_{10}$-alkyl, or $C_2$-$C_{10}$-alkenyl in a therapeutically effective amount of a non-toxic, pharmaceutically acceptable carrier.

3. The method of inducing hypothermia in mammals consisting essentially of administering cannabichromene in a therapeutically effective dosage in admixture with a non-toxic, pharmaceutically acceptable carrier.

4. A composition exhibiting antimicrobial, antiinflammatory, and hypothermia inducing therapeutic activity consisting essentially of a compound of the formula

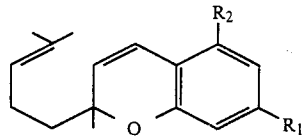

wherein $R_1$ is hydrogen, $C_1$-$C_4$-alkyl, $C_2$-$C_4$-alkenyl, $C_6$-$C_{10}$-alkyl or $C_6$-$C_{10}$-alkenyl and $R_2$ is hydroxy, or wherein $R_2$ is hydrogen, $C_1$-$C_{10}$-alkyl or $C_2$-$C_{10}$-alkenyl and $R_1$ is hydroxy and the di- or tetrahydro derivatives thereof in a therapeutically effective amount and a non-toxic pharmaceutically acceptable carrier.

5. The composition of claim 4 wherein the compound is 2-methyl-2(4'-methyl-pent-3'-enyl)-5-hydroxy-7-methyl-chromene.

6. The composition of claim 4 wherein the compound is 2-methyl-2-(4'-methyl-pent-3'-enyl)-5-methyl-7-hydrochromene.

7. The composition of claim 4 wherein the compound is 2-methyl-(4'-methyl-pent-3'-enyl)-5-hydroxy-7-methylchroman.

8. The composition of claim 4 wherein the compound is 2-methyl-2(4'-methyl-pentyl)-5-hydroxy-7-methyl-chroman.

9. The composition of claim 4 wherein the compound is 2-methyl-2-(4'-methyl-pent-3'-enyl)-5-hydrochromene.

10. The composition of claim 4 wherein the compound is 2-methyl-2(4'-methyl-pent-3'-enyl)-7-hydroxychromene.

11. The composition of claim 4 wherein the compound is 2-methyl-2(4'-methyl-pent-3'-enyl)-5-hydroxy-7-penta-dec-8'-enyl chromene.

12. The composition of claim 4 wherein the compound is 2-methyl-2(4'-methyl-pent-3'-enyl)-5-pentyl-7-hydroxychromene.

13. The composition of claim 4 wherein the compound is 2-methyl-2(4'-methyl-pentyl)-5-hydroxy-7-pentyl chroman.

14. The method of reducing inflammation in mammal comprising administering to said mammal the composition of claim 4 in a therapeutically effective concentration.

* * * * *